US010537525B2

(12) United States Patent
Faigel

(10) Patent No.: US 10,537,525 B2
(45) Date of Patent: Jan. 21, 2020

(54) METHODS AND MATERIALS FOR DELIVERING AGENTS TO LIVER TISSUE

(71) Applicant: Mayo Foundation for Medical Education and Research, Rochester, MN (US)

(72) Inventor: Douglas O. Faigel, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 138 days.

(21) Appl. No.: 15/566,037

(22) PCT Filed: Mar. 31, 2016

(86) PCT No.: PCT/US2016/025241
§ 371 (c)(1),
(2) Date: Oct. 12, 2017

(87) PCT Pub. No.: WO2016/167977
PCT Pub. Date: Oct. 20, 2016

(65) Prior Publication Data
US 2018/0133159 A1    May 17, 2018

Related U.S. Application Data

(60) Provisional application No. 62/147,208, filed on Apr. 14, 2015.

(51) Int. Cl.
*A61K 9/16*        (2006.01)
*A61K 31/337*      (2006.01)
(Continued)

(52) U.S. Cl.
CPC ............... *A61K 9/167* (2013.01); *A61B 8/12* (2013.01); *A61K 9/0019* (2013.01); *A61K 31/337* (2013.01); *A61K 31/4745* (2013.01); *A61K 31/704* (2013.01); *A61M 5/142* (2013.01); *A61M 25/0084* (2013.01);
(Continued)

(58) Field of Classification Search
CPC .. A61K 9/167; A61K 47/6929; A61K 47/643; A61K 9/0019; A61K 31/337; A61K 31/4745; A61K 31/704; A61K 35/28; A61K 45/06; A61K 9/0024; A61K 9/127; A61K 38/1709; A61P 31/00; A61B 8/12;
(Continued)

(56) References Cited

U.S. PATENT DOCUMENTS 5,964,740 A * 10/1999 Ouchi ............... A61M 25/0084
                                                604/164.01
5,979,251 A    11/1999 James et al.
(Continued)

OTHER PUBLICATIONS

Hammoud et al. [Utility of Endoscopic Ultrasound in Patient with Portal Hypertension; World Journal of Gastroenterology, vol. 20, Issue 39; Oct. 2014; pp. 14230-14236]. (Year: 2014).*
(Continued)

*Primary Examiner* — Manuel A Mendez
(74) *Attorney, Agent, or Firm* — Fish & Richardson P.C.

(57) ABSTRACT

This document provides methods and materials for delivering agents to liver tissue. For example, methods and materials for using microbeads to deliver agents (e.g., chemotherapeutic agents) to liver tissue are provided.

22 Claims, 4 Drawing Sheets

(51) Int. Cl.
| | |
|---|---|
| *A61K 31/4745* | (2006.01) |
| *A61K 31/704* | (2006.01) |
| *A61P 31/00* | (2006.01) |
| *A61B 8/12* | (2006.01) |
| *A61K 9/00* | (2006.01) |
| *A61M 5/142* | (2006.01) |
| *A61M 25/00* | (2006.01) |

(52) U.S. Cl.
CPC ...... *A61P 31/00* (2018.01); *A61M 2025/0089* (2013.01); *A61M 2210/1053* (2013.01); *A61M 2210/1057* (2013.01)

(58) Field of Classification Search
CPC ... A61M 5/142; A61M 25/0084; A61L 31/16; C12N 15/86
USPC .............................. 421/9.1, 489, 490; 607/33
See application file for complete search history.

(56) References Cited

U.S. PATENT DOCUMENTS

| | | | |
|---|---|---|---|
| 6,461,296 | B1 | 10/2002 | Desai |
| 6,486,144 | B1 | 11/2002 | Morris |
| 6,706,020 | B1 | 3/2004 | Urich |
| 6,821,013 | B2 | 11/2004 | Reilly et al. |
| 6,966,894 | B1 | 11/2005 | Urich |
| 7,060,049 | B2 | 6/2006 | Trombley, III et al. |
| 7,534,239 | B1 | 5/2009 | Schneider et al. |
| 7,771,390 | B2 | 8/2010 | Brown |
| 8,784,803 | B2 | 7/2014 | Matsuyama |
| 2005/0048040 | A1 | 3/2005 | Powers et al. |
| 2006/0251582 | A1* | 11/2006 | Reb ...................... A61K 9/5026 424/9.41 |
| 2008/0120039 | A1 | 5/2008 | Hall et al. |
| 2012/0277283 | A1 | 11/2012 | Mirkin et al. |

OTHER PUBLICATIONS

Bhutani [Endoscopic Ultrasound comes of Age; Endoscopic Ultrasound; vol. 3, Issue 3, Jul.-Sep. 2014; pp. 143-151]. (Year: 2014).*
Bhutani, "Endoscopic ultrasound comes of age: Mature, established, creative and here to stay!" Endoscopic Ultrasound, Jul.-Sep. 2014, 3(3): 143-151.
DefinityImaging.com [online], "How to Use Definity®: Using the Vialmix®," Definity Imaging, Archived on Nov. 23, 2013, retrieved on Feb. 12, 2019, <URL: http://www.definityimaging.com/how-vialmix.html>, 3 pages.
Faigel [slideshow], "EUS-guided Portal Injection Chemotherapy (EPIC) for Hepatic Metastases," EPIC Presentation Mariea-Asu, Oral Presentation, 11th EUROEUS Congress, Apr. 2014, Paris, France, 22 pages.
Faigel [slideshow], "EUS-guided Portal Injection Chemotherapy (EPIC) for Hepatic Metastases," Grant Presentation, available on or before Apr. 14, 2015, 16 pages.
Faigel et al., "Endoscopic ultrasound-guided portal injection chemotherapy for hepatic metastases," Endoscopic Ultrasound., 3(5)Supplement:1-21, Epub Mar. 27, 2014, Oral Presentation, 11th EUROEUS Congress, Paris, France, Apr. 2014, 1 page.
Faigel et al., "Mo1924 Feasibility of EUS-Guided Portal Injection of Chemotherapy (EPIC) Using Irinotecan-Loaded Microbeads for the Treatment of Hepatic Metastases," Gastroenterology, 146(5)Supplement 1:S692-S693, May 2014.
Faigel et al., [Poster], "EUS-Guided Portal Injection Chemotherapy (EPIC) for Hepatic Metastases," American Gastroenterological Association, Chicago, Illinois, May 2014, 1 pages.
Fielding et al., "Randomised controlled trial of adjuvant chemotherapy by portal-vein perfusion after curative resection for colorectal aadenocarcinoma," The Lancet, Aug. 1992, 340: 502-506.
Hammoud and Ibdah, "Utility of endoscopic ultrasound in patients with protal hypertension," World J Gastroenterology, Oct. 2014, 20(39): 14230-14236.
Imamura et al., "Sequential transcatheter arterial chemoembolization and portal vein embolization for hepatocellular carcinoma: the university of Tokyo experience," Semin Intervent Radiol., Jun. 2008, 25(2):146-154.
Kanat et al., "What is the potential role of hepatic arterial infusion chemo-therapy in the current armamentorium against colorectal cancer," J Gastrointest Oncol., Jun. 2012, 3(2):130-138.
MARIEA program awards announced, Jun. 4, 2014, 1 page.
PCT International Preliminary Report on Patentability in International Application No. PCT/US2016/025241, dated Oct. 17, 2017, 7 pages.
PCT International Search Report and Written Opinion in International Application No. PCT/US2016/025241, dated Jul. 22, 2016,.
Shindoh et al. "Portal vein embolization for hepatocellular carcinoma," Liver Cancer, Nov. 2012, 1(3-4):159-167.
Stewart, "Contrast echocardiography," Heart, Mar. 2003, 89(3): 342-348.

* cited by examiner

METHODS AND MATERIALS FOR DELIVERING AGENTS TO LIVER TISSUE

CROSS-REFERENCE TO RELATED APPLICATIONS

This application is a National Stage application under 35 U.S.C. § of International Application No. PCT/US2016/025241, having an International Filing Date of Mar. 31, 2016, which claims benefit of the U.S. Provisional Application Ser. No. 62/147,208, filed on Apr. 14, 2015. The disclosure of the prior applications are considered part of the disclosure of this application, and incorporated in its entirety into this application.

BACKGROUND

1. Technical Field

This document relates to methods and materials for delivering agents to liver tissue. For example, this document relates to methods and materials for using endoscopic ultrasound to deliver agents (e.g., chemotherapeutic agents) to liver tissue.

2. Background Information

The liver is a common site of primary and metastatic malignancies. Multiple sites of disease within the liver are common and prevent the use of directed therapies such as radiofrequency ablation (RFA), transarterial chemoembolization (TACE), and resection. In these cases, systemic chemotherapy is given, but its efficacy may be limited by systemic toxicities that do not allow an adequate dose to be achieved in the liver.

SUMMARY

This document provides methods and materials for delivering agents to liver tissue. For example, this document provides methods and materials for using endoscopic ultrasound to deliver agents (e.g., chemotherapeutic agents loaded onto microbeads) to liver tissue. As described herein, agents can be administered to the portal vein of a mammal (e.g., a human) in a manner that allows the agent to travel to portal venules of the liver where they can be trapped and remain while the agent is slowly released over time. In some cases, the agents such as microbeads can be administered as described herein in a manner that allows the agent to be substantially evenly distributed within liver tissue, that allows for higher concentrations of the delivered agent within liver tissue than is achieved by administering the same amount of agent systemically (e.g., intravenously), and/or that allows a lower concentration of the delivered agent within non-liver tissues of the periphery (e.g., bone marrow, heart, intestine, muscle, or skin) than is achieved by administering the same amount of agent systemically (e.g., intravenously).

In general, one aspect of this document features a method for delivering an agent to liver tissue. The method comprises, or consists essentially of, (a) advancing an endoscope device configured with a needle into the stomach or duodenum of a mammal under endoscopic ultrasound guidance, (b) advancing the needle out of the stomach or duodenum and into a portal vein of the mammal, and (c) administering a solution containing the agent into the portal vein, wherein the concentration of the agent within liver tissue of the mammal following the administering step is greater than the concentration of the agent within liver tissue when the same amount of the agent is administered to the jugular vein of a control mammal. The mammal can be a human. The agent can be irinotecan, doxorubicin, or paclitaxel. The solution can comprise the agent loaded onto microbeads having a diameter between about 75 μm and about 700 μm. The concentration of the agent within plasma of the mammal 30 minutes following the administering step can be less than the concentration of the agent within plasma 30 minutes after the same amount of the agent is administered to the jugular vein of a control mammal without microbeads. The solution can be administered to the portal vein through the needle. The endoscope device can comprise a catheter. The catheter can be advanced over the needle into the portal vein; the needle can be removed from the portal vein; and the solution can be administered to the portal vein through the catheter. The catheter can be advanced through the needle into the portal vein; the needle can be removed from the portal vein; and the solution can be administered to the portal vein through the catheter. The endoscope device can comprise a pump configured to move the solution through the endoscope device and into the portal vein. The solution can comprise the agent loaded onto microbeads; and the pump can be configured to agitate the solution while within the endoscope device to minimize the settling out of the microbeads from the solution.

In another aspect, this document features a method for delivering an agent to liver tissue. The method comprises, or consists essentially of, (a) advancing an endoscope device configured with a needle into the stomach or duodenum of a mammal under endoscopic ultrasound guidance, (b) advancing the needle out of the stomach or duodenum and into a portal vein of the mammal, and (c) administering a solution containing microbeads comprising the agent into the portal vein, wherein the concentration of the agent within liver tissue of the mammal following the administering step is greater than the concentration of the agent within liver tissue when the same amount of the agent is administered to the jugular vein of a control mammal without microbeads. The mammal can be a human. The agent can be irinotecan, doxorubicin, or paclitaxel. The microbeads can have a diameter between about 75 μm and about 700 μm. The concentration of the agent within plasma of the mammal 30 minutes following the administering step can be less than the concentration of the agent within plasma 30 minutes after the same amount of the agent is administered to the jugular vein of a control mammal without microbeads. The solution can be administered to the portal vein through the needle. The endoscope device can comprise a catheter. The catheter can be advanced over the needle into the portal vein; the needle can be removed from the portal vein; and the solution can be administered to the portal vein through the catheter. The catheter can be advanced through the needle into the portal vein; the needle can be removed from the portal vein; and the solution can be administered to the portal vein through the catheter. The endoscope device can comprise a pump configured to move the solution through the endoscope device and into the portal vein. The pump can be configured to agitate the solution while within the endoscope device to minimize the settling out of the microbeads from the solution.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials for delivering agents to liver tissue. For example, this document provides methods and materials for using endoscopic ultrasound-guided portal vein injection of microbeads loaded with one or more agents (e.g., chemotherapeutic agents) to deliver the agents to liver tissue of a mammal. In some cases, the methods and materials provided herein can be used to treat cancer. For example, microbeads loaded with one or more agents (e.g., chemotherapeutic agents) can be administered as described herein to treat liver cancer or other cancers located within liver tissue such as metastatic breast cancer, metastatic colorectal cancer, metastatic pancreas cancer, or metastatic lung cancer. In some cases, the methods and materials provided herein can be used to administer agents (e.g., chemotherapeutic agents) that do not require microbeads such as albumin-bound paclitaxel nanoparticles. In some cases, the methods and materials provided herein can be used to treat cancer present in liver tissue in any appropriate type of mammal including, without limitation, mice, rats, dogs, cats, horses, cattle, pigs, monkeys, and humans.

Any appropriate agent (e.g., chemotherapeutic agent) or combination of agents (e.g., two, three, four, five, six, seven, or more chemotherapeutic agents) can be loaded onto microbeads and administered to a mammal as described herein. Examples of chemotherapeutic agents that can be loaded onto microbeads and administered to a mammal as described herein include, without limitation, irinotecan ((S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate) and doxorubicin ((7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione). Examples of agents that can be administered as described herein without being loaded onto microbeads include, without limitation, albumin-bound paclitaxel particles, doxorubicin liposomal preparations, oxaliplatin, fluorouracil, and gemcitabine.

Any appropriate microbead can be loaded with one or more agents and administered to a mammal as described herein. For example, microbeads made of polyvinyl alcohol or sulphonate modified N-Fil hydrogel can be loaded with one or more agents and administered to a mammal as described herein. In some cases, the microbeads can have a diameter ranging from about 70 µm to about 700 µm (e.g., from about 75 µm to about 700 µm, from about 70 µm to about 500 µm, from about 70 µm to about 300 µm, from about 70 µm to about 150 µm, from about 100 µm to about 700 µm, from about 300 µm to about 700 µm from about 500 µm to about 700 µm, from about 70 µm to about 150 µm, from about 100 µm to about 300 µm, or from about 300 µm to about 500 µm).

Figure 1:
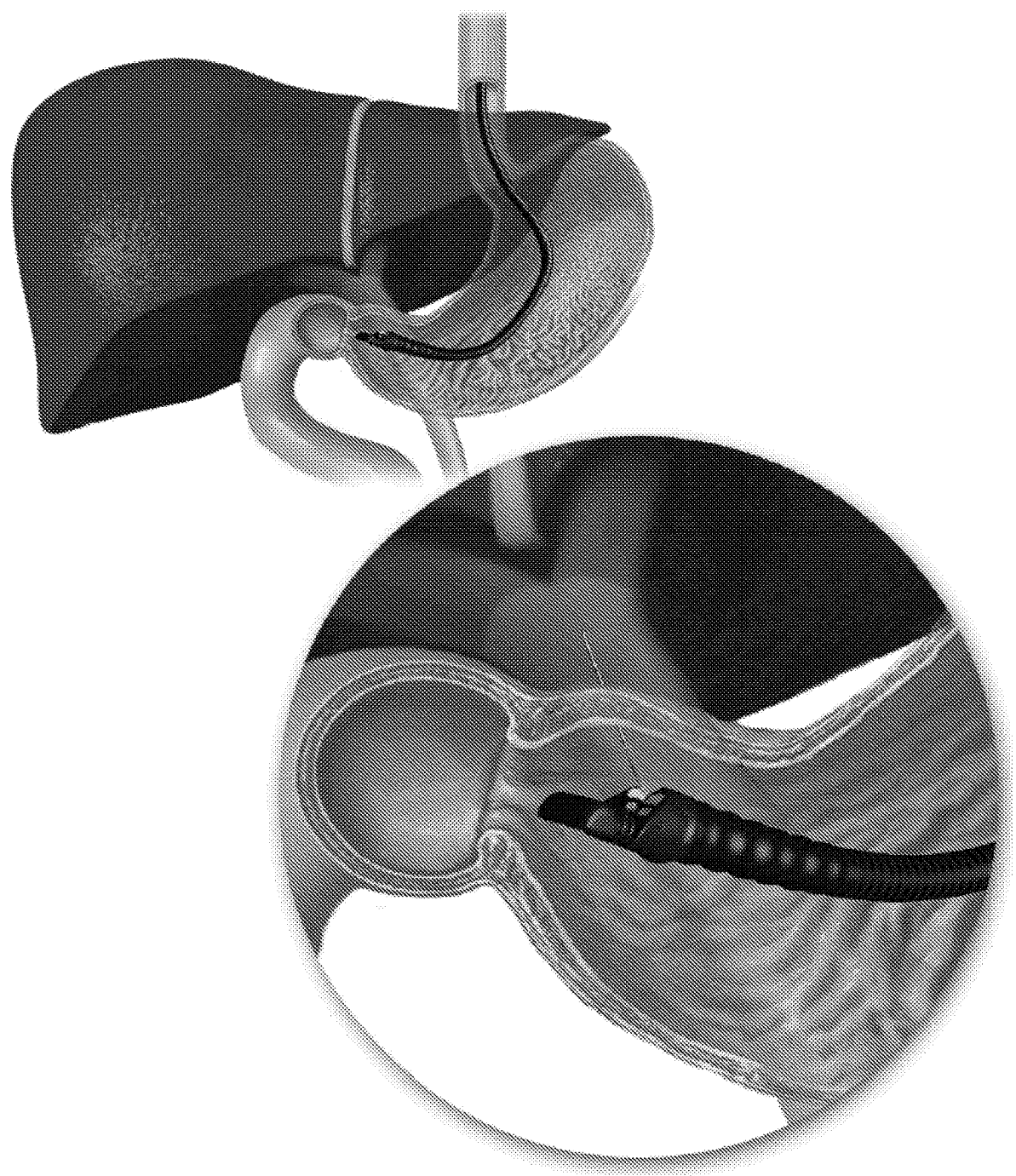
FIG. 1 is a diagram of an echoendoscope being advanced through the stomach to provide access to a portal vein. A needle is shown being advanced across the stomach wall and into the portal vein.
Figure 2:
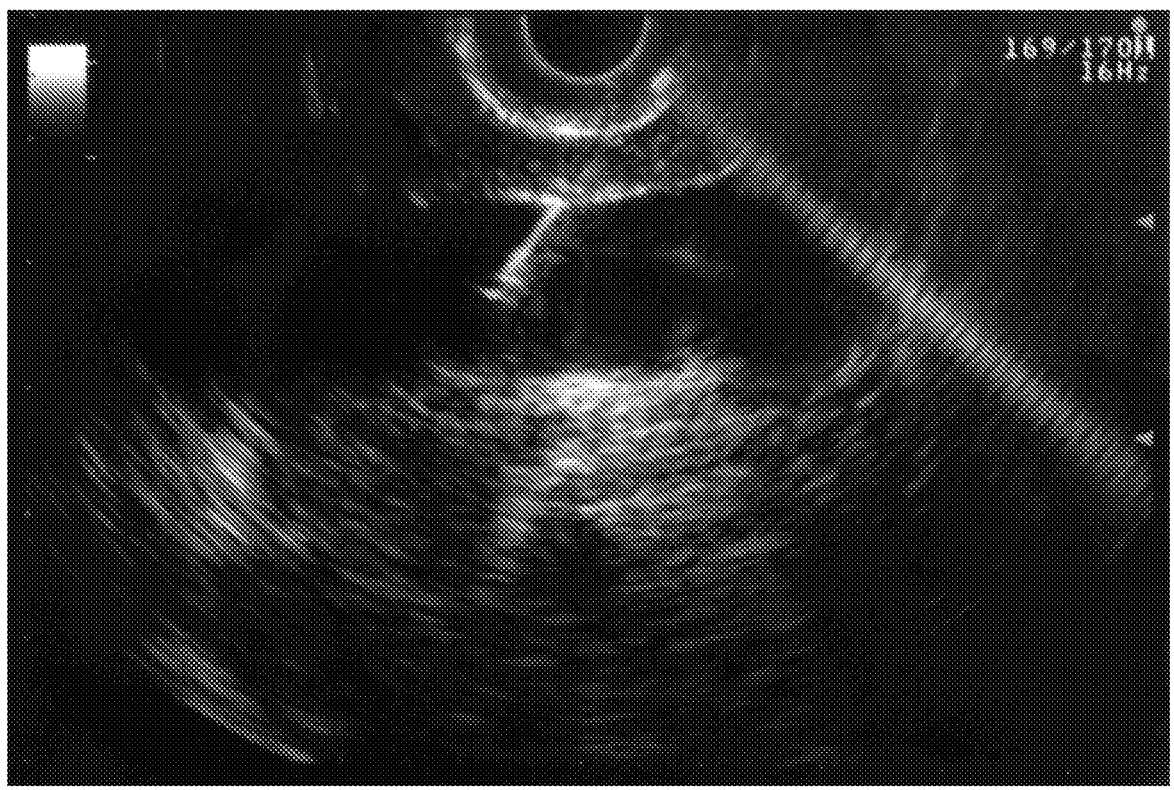
FIG. 2 is a photograph of an ultrasound imaging showing the needle within the portal vein of a mammal (pig).
Figure 3:
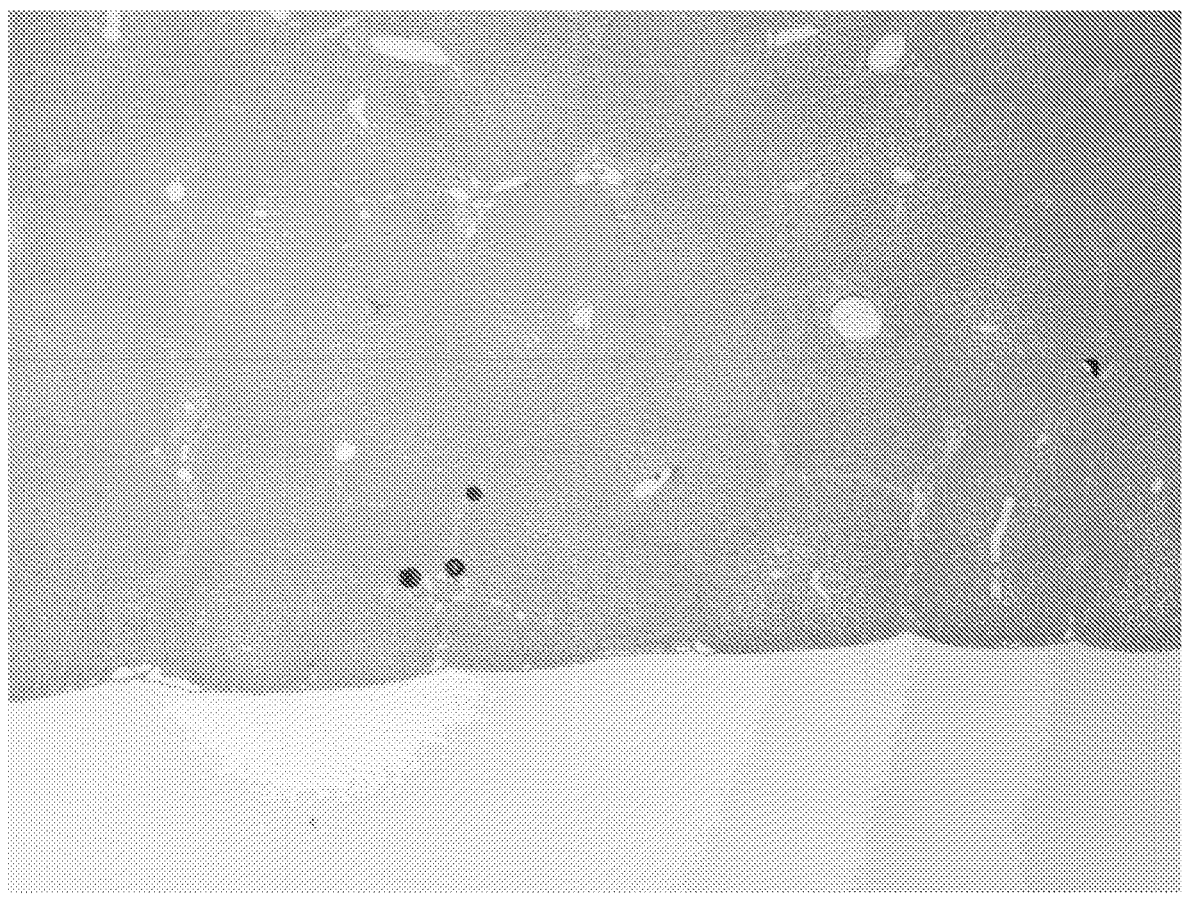
FIG. 3 is a photomicrograph (1.25×) demonstrating drug-eluting microbeads trapped in a hepatic portal venule after endoscopic ultrasound-guided injection.
Figure 4:
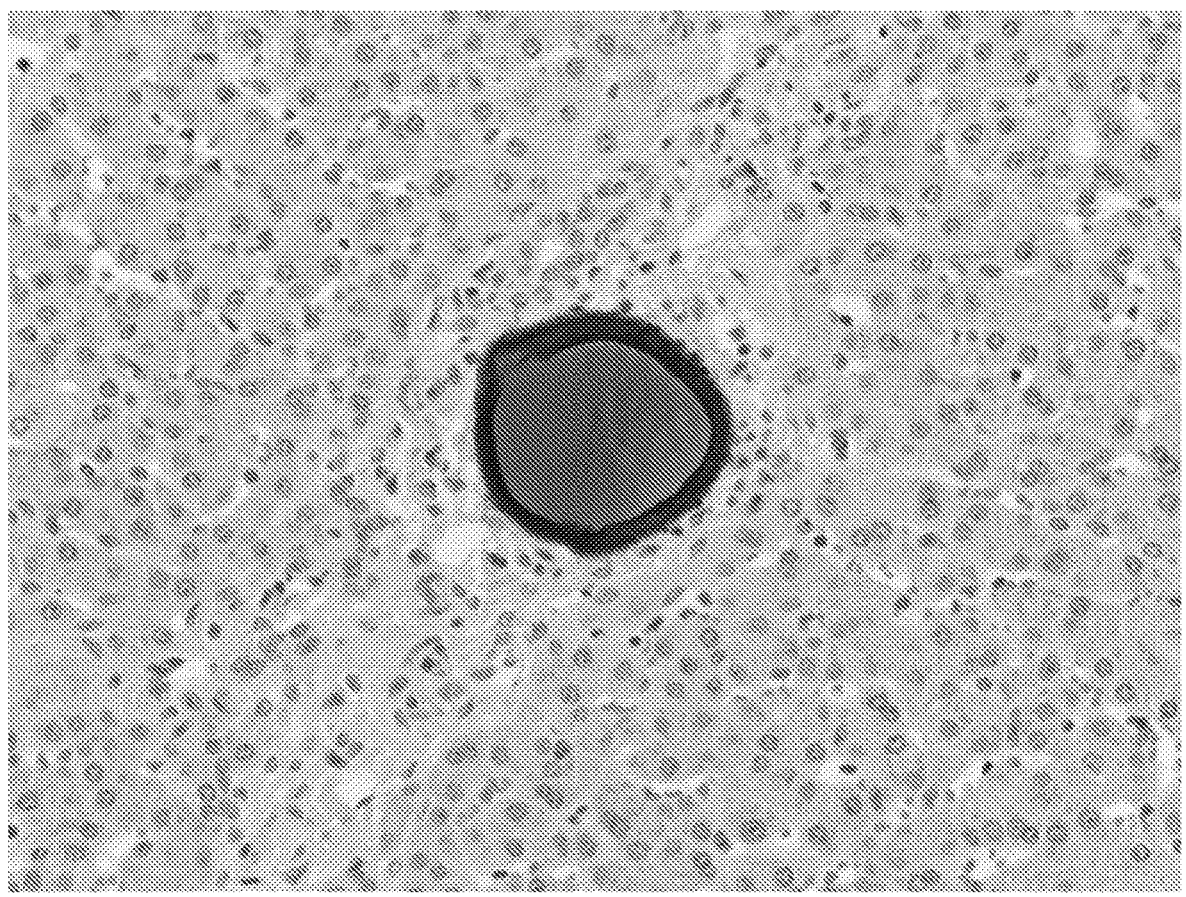
FIG. 4 is a photomicrograph (20×) demonstrating a drug-eluting microbead trapped in a hepatic portal venule after endoscopic ultrasound-guided injection.

Any appropriate method can be used to administer microbeads loaded with one or more agents to a portal vein of a mammal (e.g., a human). For example, endoscopic ultrasound-guided techniques can be used to insert a needle into the portal vein of a mammal transgastrically to administer microbeads loaded with one or more agents (FIGS. 1 and 2). In some cases, an echoendoscope such as an Olympus linear array echoendoscope can be used. The portal vein can be identified by location, appearance, and/or a pulse-wave Dopper signature. Any appropriate endoscopic ultrasound-compatible needle can be used to enter the portal vein. For example, 22 gauge stainless steel fine-needle aspiration needle such as those provided by Cook Medical can be advanced transgastrically into the portal vein. In some cases, the needle can have a gauge ranging from about 25 to about 19.

In some cases, a needle can be designed to include a plastic catheter that is inserted over the endoscopic ultrasound-compatible needle or advanced through the endoscopic ultrasound-compatible needle. Such a catheter can be less thrombogenic and less prone to injuring vessels than stainless steel needles lacking a plastic catheter. In some cases, the use of a plastic catheter can allow for longer injection times, which can lead to lower peak drug concentrations and less drug toxicity. When using a needle configuration having a plastic catheter located over the needle, the portal vein can be punctured, and the internal needle can be withdrawn leaving only the plastic catheter in place in the portal vein. Such a process can be controlled using a needle handle assembly configured to actuate withdrawal of the needle, while leaving the outer plastic catheter in place.

When using a needle configuration having a plastic catheter located within the needle, the portal vein can be punctured, and an inner catheter can be advanced through the needle and into the portal vein. At this point, the needle can be withdrawn, and the microbeads can be injected into the portal vein through the catheter. Such a process can be controlled using a needle handle assembly configured to advance an inner catheter, withdraw the outer needle, and administer a solution containing microbeads into the portal vein through the catheter. In some cases, the inner catheter can be positioned within the needle prior to insertion into the mammal or prior to insertion into the portal vein.

A pump can be used to infuse a solution containing microbeads loaded with one or more agents into the portal vein of a mammal. In some cases, the pump can be configured to agitate the solution located within the lumen of an endoscope used to deliver the solution to the portal vein of a mammal. This lumen can be from about 1.0 m to about 2.0 m in length (e.g., about 1.5 m in length). In some cases, this agitation can help maintain the microbeads or other agents in suspension during the injection, thereby providing a consistent rate of injection over time and an even distribution of microbeads and agents within liver tissue. Examples of syringe pumps and agitation devices configured to agitate a solution being injected that can be used as described herein include, without limitation, those described in U.S. Pat. Nos. 7,771,390, 7,534,239, and 6,966,894.

In some cases, the pump can be programmable to control the duration of injection. For example, a pump can be configured to allow a user to program an infusion rate such that a particular dose of microbeads loaded with one or more agents is infused into the portal vein of a mammal over from about 1 minute to about 30 minutes (e.g., from about 2 minutes to about 30 minutes, from about 5 minutes to about 30 minutes, from about 10 minutes to about 30 minutes, from about 2 minutes to about 20 minutes, from about 2 minutes to about 15 minutes, from about 5 minutes to about 30 minutes, from about 10 minutes to about 30 minutes, from about 5 minutes to about 15 minutes, or from about 5 minutes to about 10 minutes). In some cases, the pump can be configured to have a kill switch to instantly halt injection, for example, in those cases where there is extravasation.

In some cases, the methods and materials provided herein can be used to deliver a solution to other locations within a mammal. For example, endoscopic ultrasound-guided techniques can be used to deliver a solution containing microbeads loaded with one or more agent or a solution lacking microbeads to a lung, kidney, brain, bone, pancreas, or bowel. In some cases, the methods and materials provided herein can be used during an interventional radiology treatment such as chemoembolization or direct injection chemotherapy into a tumor.

The invention will be further described in the following examples, which do not limit the scope of the invention described in the claims.

EXAMPLES

Example 1

Endoscopic Ultrasound-Guided Portal Vein Injection Chemotherapy for Hepatic Metastases The following was performed to assess the use of endoscopic ultrasound-guided portal vein injection of irinotecan loaded microbeads to achieve increased intrahepatic concentrations of irinotecan while decreasing systemic irinotecan exposure.

Endoscopic ultrasound-guided portal vein injections were administered to 8 anesthetized 35 kg pigs transgastrically using a linear array echoendoscope and a 22 gauge fine-needle aspiration needle. Briefly, an Olympus linear array echoendoscope was inserted perorally to the stomach. The portal vein was identified by location, appearance, and pulse-wave Dopper signature. A 22 gauge fine-needle aspiration needle (Cook Medical) was advanced transgastrically into the portal vein.

In 4 animals, irinotecan (100 mg) loaded onto 75-150 micron LC Beads® (Biocompatibles UK LTD) was injected. In 4 animals, saline was injected into the portal vein, and unloaded irinotecan (100 mg) was injected into the jugular vein. Plasma was collected at baseline and every 15 minutes for one hour. At 1 hour, laparotomy was performed, and liver and skeletal muscle samples were obtained and frozen. Bone marrow aspirates were obtained at one hour from the right anterior tibia. Irinotecan and SN-38 (active metabolite) concentrations were determined using LC/MS.

The procedure was performed safely in all 8 animals. Compared to systemic administration, the endoscopic ultrasound-guided portal vein injections of irinotecan loaded microbeads resulted in almost twice the hepatic concentration of irinotecan (6242 vs. 3692 ng/gm) and half the systemic concentrations in plasma (1092 vs. 2762 ng/mL), bone marrow (815 vs. 1703 ng/mL), and skeletal muscle (521 vs. 1058 ng/gm) (Table 1). SN38 levels were lower with the endoscopic ultrasound-guided portal vein injections of irinotecan loaded microbeads (Liver: 166 vs. 681 ng/gm; plasma: 1.8 vs. 2.4 ng/mL; bone marrow: 0.9 vs. 1.4 ng/mL; and muscle 4.6 vs. 9.2 ng/gm). Liver histology revealed that the microbeads were within small portal venules (FIG. 1).

TABLE 1

Plasma and tissue concentrations (ng/mL or ng/g).

| | Peak Plasma | Bone Marrow | Muscle | Liver |
|---|---|---|---|---|
| Irinotecan levels following portal vein injection of Irinotecan-containing microbeads: | 1092 | 815 | 521 | 6242 |
| Irinotecan levels following control injection of Irinotecan: | 2762 | 1703 | 1058 | 3692 |
| SN38 levels following portal vein injection of Irinotecan-containing microbeads: | 1.8 | 0.9 | 4.6 | 166 |
| SN38 levels following control injection of Irinotecan: | 2.4 | 1.4 | 9.2 | 681 |

These results demonstrate that portal vein injection of irinotecan-loaded microbeads can enhance hepatic exposure to irinotecan, while decreasing systemic concentrations. SN38 levels were lower with the portal vein injection of irinotecan-loaded microbeads, indicating that a substantial portion of the irinotecan was still loaded on the microbeads. These results demonstrate that the microbeads may act as a reservoir resulting in prolonged hepatic drug exposure.

Example 2

Endoscopic Ultrasound-Guided Portal Vein Injection Chemotherapy for Hepatic Metastases The following was performed to assess the use of endoscopic ultrasound-guided portal vein injection of doxorubicin loaded microbeads to achieve increased intrahepatic concentrations of doxorubicin while decreasing systemic doxorubicin exposure. Doxorubicin is a cardiotoxic agent.

Endoscopic ultrasound-guided portal vein injections were administered to 8 anesthetized 35 kg pigs transgastrically using a linear array echoendoscope and a 22 gauge fine-needle aspiration needle. Briefly, an Olympus linear array echoendoscope was inserted perorally to the stomach. The portal vein was identified by location, appearance, and pulse-wave Dopper signature. A 22 gauge fine-needle aspiration needle (Cook Medical) was advanced transgastrically into the portal vein.

In 4 animals, doxorubicin (100 mg) loaded onto 75-150 micron LC Beads® (Biocompatibles UK LTD) was injected. In 4 animals, saline was injected into the portal vein, and unloaded doxorubicin (100 mg) was injected into the jugular vein. Plasma was collected at baseline and every 15 minutes for one hour. At 1 hour, laparotomy was performed, and liver and heart samples were obtained and frozen. Bone marrow aspirates were obtained at one hour from the right anterior tibia. Doxorubicin concentrations were determined using LC/MS.

The procedure was performed safely in all 8 animals. Compared to systemic administration, the endoscopic ultrasound-guided portal vein injections of doxorubicin loaded microbeads resulted in a 5-fold increase in hepatic doxorubicin levels, a 30-fold decrease in heart doxorubicin levels, a 500-fold decrease in peak plasma doxorubicin levels, and a 6-fold decrease in bone marrow doxorubicin levels (Table 2). The results were significant ($p<0.05$).

TABLE 2

Plasma and tissue concentrations (ng/mL or ng/g).

|  | Peak Plasma | Bone Marrow | Heart | Liver |
|---|---|---|---|---|
| Doxorubicin levels following portal vein injection of doxorubicin-containing microbeads: | 4.3 | 3.6 | 153 | 35450 |
| Doxorubicin levels following control injection of doxorubicin: | 2041 | 25 | 4805 | 6930 |

These results demonstrate that portal vein injection of doxorubicin-loaded microbeads can enhance hepatic exposure to doxorubicin, while decreasing systemic concentrations. These results demonstrate that the doxorubicin loaded microbeads may act as a reservoir resulting in prolonged hepatic drug exposure.

Example 3

Endoscopic Ultrasound-Guided Portal Vein Injection Chemotherapy for Hepatic Metastases The following was performed to assess the use of endoscopic ultrasound-guided portal vein injection of albumin-bound paclitaxel nanoparticles to achieve increased intrahepatic concentrations of paclitaxel while decreasing systemic paclitaxel exposure.

Endoscopic ultrasound-guided portal vein injections were administered to 8 anesthetized 35 kg pigs transgastrically using a linear array echoendoscope and a 22 gauge fine-needle aspiration needle. Briefly, an Olympus linear array echoendoscope was inserted perorally to the stomach. The portal vein was identified by location, appearance, and pulse-wave Dopper signature. A 22 gauge fine-needle aspiration needle (Cook Medical) was advanced transgastrically into the portal vein.

In 4 animals, albumin bound paclitaxel nanoparticles (100 mg; Abraxane, Summit, N.J.) was injected. In 4 animals, saline was injected into the portal vein, and albumin bound paclitaxel nanoparticles (100 mg; Abraxane, Summit, N.J.) was injected into the jugular vein. Plasma was collected at baseline and every 15 minutes for one hour. At 1 hour, laparotomy was performed, and liver and muscle samples were obtained and frozen. Bone marrow aspirates were obtained at one hour from the right anterior tibia. Paclitaxel concentrations were determined using LC/MS.

The procedure was performed safely in all 8 animals. Compared to systemic administration, the endoscopic ultrasound-guided portal vein injections of albumin bound paclitaxel nanoparticles increased hepatic concentrations of paclitaxel by 60% and decreased systemic levels by 24-32% (Table 3).

TABLE 3

Plasma and tissue concentrations (ng/mL or ng/g).

|  | Peak Plasma | Bone Marrow | Muscle | Liver |
|---|---|---|---|---|
| Paclitaxel levels following portal vein injection | 658 | 155 | 433 | 17327 |

TABLE 3-continued

Plasma and tissue concentrations (ng/mL or ng/g).

|  | Peak Plasma | Bone Marrow | Muscle | Liver |
|---|---|---|---|---|
| Paclitaxel levels following control injection | 864 | 224 | 635 | 10854 |

Example 4

Endoscopic Ultrasound-Guided Portal Vein Injections

As described herein, endoscopic ultrasound-guided injections into the portal vein in the acute porcine model resulted in a doubling of hepatic irinotecan levels, 5-fold increase in hepatic doxorubicin levels, and substantial decreases in systemic levels including a 30-fold decrease in cardiac doxorubicin levels at one hour as compared to systemic injection. The following was performed to assess the safety and toxicity of endoscopic ultrasound-guided injections in the survival porcine model. The aim was to determine 7-day safety, toxicity, and drug levels in the survival porcine model of endoscopic ultrasound-guided injections using irinotecan and doxorubicin loaded onto microbeads, as compared with systemic injection.

Sixteen anesthetized 35 kg male pigs were treated with 50 mg of either irinotecan (n=8) or doxorubicin (n=8). This dose was chosen to approximate half the usual human dosage, given the increased hepatic levels demonstrated herein, and to represent the expected starting dose in subsequent phase one dose escalation human trials. Within each drug group, half (n=4) were treated with endoscopic ultrasound-guided injections using 75-150 micron LC Beads (Biocompatibles) or endoscopic ultrasound-guided injection of drug not loaded onto microbeads into the IVC, using 22g endoscopic ultrasound needles via a transgastric approach. Each animal received only one drug by one route. Animals were observed twice daily for 7 days for clinical signs of toxicity. Whole blood for cell counts and plasma chemistries were obtained at baseline and at 7 days. All animals were sacrificed at seven days, and necropsy performed to obtain tissue for histological examination (liver, bone marrow, intestine, heart). 7 day drug levels were measured by LC-mass spectometry on plasma, bone marrow, liver and heart.

No clinical toxicities were observed. All animals behaved, ate, and drank normally during the 7 day observation period. There were no changes in electrolytes, glucose, Hct, WBC count, or LFTs. Liver histology showed mild changes in both groups and mild foreign body reactions around the beads. No significant histological changes were seen in the other tissue sites. There was no detectable irinotecan or SN-38 (active metabolite of irinotecan) at 7 days in any samples. For doxorubicin, no drug was detected in the plasma or bone marrow of either group, and the mean (SD) hepatic levels were similar (181 (241) vs 151 (67) ng/gm, endoscopic ultrasound-guided portal injection chemotherapy vs control, p=NS). Doxorubicin mean (SD) levels in the heart were significantly lower in the endoscopic ultrasound-guided portal injection chemotherapy versus control groups (15 (4) vs. 138 (48) ng/gm, p=0.015).

Endoscopic ultrasound-guided portal injection chemotherapy using drug eluting microbeads was safe and well tolerated with no significant toxicities at the dosages used.

There was no detectable irinotecan or its active metabolite SN-38 at 7 days in plasma or tissues. Hepatic levels of doxorubicin at 7 days were similar between groups, but cardiac levels were significantly lower in the endoscopic ultrasound-guided portal injection chemotherapy group, a potentially important advantage given the cardiotoxicity of doxorubicin.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for delivering an agent to liver tissue, wherein said method comprises:
    (a) advancing an endoscope device configured with a needle into the stomach or duodenum of a mammal under endoscopic ultrasound guidance,
    (b) advancing said needle out of said stomach or duodenum and into a portal vein of said mammal, and
    (c) administering a solution containing said agent into said portal vein,
    wherein the concentration of said agent within liver tissue of said mammal following said administering step is greater than the concentration of said agent within liver tissue when the same amount of said agent is administered to the jugular vein of a control mammal.

2. The method of claim 1, wherein said mammal is a human.

3. The method of claim 1, wherein said agent is irinotecan, doxorubicin, or paclitaxel.

4. The method of claim 1, wherein said solution comprises said agent loaded onto microbeads having a diameter between about 75 μm and about 700 μm.

5. The method of claim 4, wherein the concentration of said agent within plasma of said mammal 30 minutes following said administering step is less than the concentration of said agent within plasma 30 minutes after the same amount of said agent is administered to the jugular vein of a control mammal without microbeads.

6. The method of claim 1, wherein said solution is administered to said portal vein through said needle.

7. The method of claim 1, wherein said endoscope device comprises a catheter.

8. The method of claim 7, wherein said catheter is advanced over said needle into said portal vein, wherein said needle is removed from said portal vein, and wherein said solution is administered to said portal vein through said catheter.

9. The method of claim 7, wherein said catheter is advanced through said needle into said portal vein, wherein said needle is removed from said portal vein, and wherein said solution is administered to said portal vein through said catheter.

10. The method of claim 1, wherein said endoscope device comprises a pump configured to move said solution through said endoscope device and into said portal vein.

11. The method of claim 10, wherein said solution comprises said agent loaded onto microbeads, and wherein said pump is configured to agitate said solution while within said endoscope device to minimize the settling out of said microbeads from said solution.

12. A method for delivering an agent to liver tissue, wherein said method comprises:
    (a) advancing an endoscope device configured with a needle into the stomach or duodenum of a mammal under endoscopic ultrasound guidance,
    (b) advancing said needle out of said stomach or duodenum and into a portal vein of said mammal, and
    (c) administering a solution containing microbeads comprising said agent into said portal vein,
    wherein the concentration of said agent within liver tissue of said mammal following said administering step is greater than the concentration of said agent within liver tissue when the same amount of said agent is administered to the jugular vein of a control mammal without microbeads.

13. The method of claim 12, wherein said mammal is a human.

14. The method of claim 12, wherein said agent is irinotecan, doxorubicin, or paclitaxel.

15. The method of claim 12, wherein said microbeads have a diameter between about 75 μm and about 700 μm.

16. The method of claim 12, wherein the concentration of said agent within plasma of said mammal 30 minutes following said administering step is less than the concentration of said agent within plasma 30 minutes after the same amount of said agent is administered to the jugular vein of a control mammal without microbeads.

17. The method of claim 12, wherein said solution is administered to said portal vein through said needle.

18. The method of claim 12, wherein said endoscope device comprises a catheter.

19. The method of claim 18, wherein said catheter is advanced over said needle into said portal vein, wherein said needle is removed from said portal vein, and wherein said solution is administered to said portal vein through said catheter.

20. The method of claim 18, wherein said catheter is advanced through said needle into said portal vein, wherein said needle is removed from said portal vein, and wherein said solution is administered to said portal vein through said catheter.

21. The method of claim 12, wherein said endoscope device comprises a pump configured to move said solution through said endoscope device and into said portal vein.

22. The method of claim 21, wherein said pump is configured to agitate said solution while within said endoscope device to minimize the settling out of said microbeads from said solution.

* * * * *